(12) United States Patent
Viola et al.

(10) Patent No.: US 10,537,371 B2
(45) Date of Patent: Jan. 21, 2020

(54) WRIST PLATE AND DRILL GUIDE

(71) Applicant: OsteoMed LLC, Addison, TX (US)

(72) Inventors: Randall W. Viola, Vail, CO (US);
Nicholas Monks, Frisco, TX (US);
Joseph Pepin, Sachse, TX (US);
Eduardo Franco, The Colony, TX (US)

(73) Assignee: OsteoMed LLC, Addison, TX (US)

( * ) Notice: Subject to any disclaimer, the term of this patent is extended or adjusted under 35 U.S.C. 154(b) by 479 days.

(21) Appl. No.: 15/389,356

(22) Filed: Dec. 22, 2016

(65) Prior Publication Data

US 2017/0181782 A1 Jun. 29, 2017

Related U.S. Application Data

(60) Provisional application No. 62/387,231, filed on Dec. 23, 2015.

(51) Int. Cl.
*A61B 17/80* (2006.01)
*A61B 17/88* (2006.01)

(52) U.S. Cl.
CPC ...... *A61B 17/8061* (2013.01); *A61B 17/8897* (2013.01)

(58) Field of Classification Search
CPC . A61B 17/1728; A61B 17/80; A61B 17/8028; A61B 17/8052; A61B 17/8057; A61B 17/8061
See application file for complete search history.

(56) References Cited

U.S. PATENT DOCUMENTS

| 4,465,065 A | * | 8/1984 | Gotfried | A61B 17/1721 606/65 |
| 6,916,323 B2 | * | 7/2005 | Kitchens | A61B 17/1725 606/104 |
| 7,563,263 B2 | * | 7/2009 | Orbay | A61B 17/1728 606/62 |
| 7,727,236 B2 | * | 6/2010 | Choe | A61B 17/1633 606/86 R |
| 7,837,689 B2 | * | 11/2010 | Leyden | A61B 17/1728 606/280 |
| 8,043,297 B2 | * | 10/2011 | Grady, Jr. | A61B 17/1728 606/98 |
| 8,100,952 B2 | * | 1/2012 | Matityahu | A61B 17/80 606/280 |

(Continued)

*Primary Examiner* — Eric S Gibson
(74) *Attorney, Agent, or Firm* — Norton Rose Fulbright US LLP

(57) ABSTRACT

The present disclosure describes various embodiments of a plate and guide that enable fixation of a fractured bone while reducing damage to tissue in the vicinity of the fractured bone. The plate may be sized and dimensioned such that the plate may be slid underneath a muscle or other tissue and positioned into a proper location for providing fixation of the plate to the fractured bone without requiring cutting of the muscle or other tissue. The guide may be sized and dimensioned to interface with the plate such that the guide is place over the top of the muscle or other tissue, thereby enabling the guide to be used for providing screws or other devices (e.g., rods, K-wires, etc.) to the plate in a proper orientation to provide fixation to the fractured bone without requiring cutting of the muscle or other tissue.

20 Claims, 13 Drawing Sheets

(56) References Cited

U.S. PATENT DOCUMENTS

| | | | |
|---|---|---|---|
| 8,403,967 B2 * | 3/2013 | Orbay | A61B 17/1728 606/281 |
| 8,439,932 B2 * | 5/2013 | Sheffer | A61B 17/1728 606/104 |
| 9,089,375 B2 * | 7/2015 | Smith | A61B 17/1725 |
| 9,480,512 B2 * | 11/2016 | Orbay | A61B 17/1728 |
| 9,492,213 B2 * | 11/2016 | Orbay | A61B 17/1728 |
| 9,572,609 B2 * | 2/2017 | Orbay | A61B 17/1728 |
| 10,368,928 B2 * | 8/2019 | Lueth | A61B 17/1728 |
| 2004/0153073 A1 * | 8/2004 | Orbay | A61B 17/1728 606/291 |
| 2005/0159747 A1 * | 7/2005 | Orbay | A61B 17/1728 606/86 B |
| 2005/0245931 A1 * | 11/2005 | Orbay | A61B 17/1728 606/291 |
| 2005/0283154 A1 * | 12/2005 | Orbay | A61B 17/1728 606/62 |
| 2006/0095044 A1 * | 5/2006 | Grady, Jr. | A61B 17/1728 606/96 |
| 2007/0173843 A1 * | 7/2007 | Matityahu | A61B 17/80 606/916 |
| 2007/0276401 A1 * | 11/2007 | Choe | A61B 17/1633 606/96 |
| 2008/0140130 A1 * | 6/2008 | Chan | A61B 17/1728 606/280 |
| 2009/0076554 A1 * | 3/2009 | Huebner | A61B 17/1684 606/280 |
| 2009/0088767 A1 * | 4/2009 | Leyden | A61B 17/1721 606/96 |
| 2010/0137873 A1 * | 6/2010 | Grady, Jr. | A61B 17/1728 606/96 |
| 2010/0268283 A1 * | 10/2010 | Orbay | A61B 17/1728 606/281 |
| 2011/0270319 A1 * | 11/2011 | Sheffer | A61B 17/1728 606/280 |
| 2013/0072988 A1 * | 3/2013 | Hulliger | A61B 17/1728 606/281 |
| 2013/0079829 A1 * | 3/2013 | Globerman | A61B 17/8033 606/286 |
| 2013/0204305 A1 * | 8/2013 | Orbay | A61B 17/1728 606/281 |
| 2013/0245699 A1 * | 9/2013 | Orbay | A61B 17/8061 606/286 |
| 2014/0100615 A1 * | 4/2014 | Orbay | A61B 17/1728 606/286 |
| 2014/0128871 A1 * | 5/2014 | Orbay | A61B 17/1728 606/71 |
| 2014/0371799 A1 * | 12/2014 | Sixto | A61B 17/8057 606/281 |
| 2015/0105779 A1 * | 4/2015 | Smith | A61B 17/1725 606/71 |
| 2016/0324552 A1 * | 11/2016 | Baker | A61B 17/1728 |
| 2016/0374738 A1 * | 12/2016 | Smith | A61B 17/725 606/71 |
| 2017/0049493 A1 * | 2/2017 | Gauneau | A61B 17/8872 |
| 2017/0056082 A1 * | 3/2017 | Orbay | A61B 17/1728 |
| 2017/0181782 A1 * | 6/2017 | Viola | A61B 17/1728 |
| 2017/0209195 A1 * | 7/2017 | Chick | A61B 17/8061 |
| 2018/0000496 A1 * | 1/2018 | Langdale | A61B 17/8052 |
| 2018/0049787 A1 * | 2/2018 | Davison | B29C 70/46 |
| 2018/0199950 A1 * | 7/2018 | Mebarak | A61B 17/1728 |
| 2018/0256222 A1 * | 9/2018 | Lueth | A61B 17/8014 |
| 2018/0256223 A1 * | 9/2018 | Lueth | A61B 17/8014 |
| 2018/0289402 A1 * | 10/2018 | Lueth | A61B 17/1728 |
| 2019/0076174 A1 * | 3/2019 | Tiongson | A61B 17/808 |
| 2019/0076177 A1 * | 3/2019 | Tiongson | A61B 17/8085 |
| 2019/0133611 A1 * | 5/2019 | Schreiber | A61B 17/1728 |

* cited by examiner

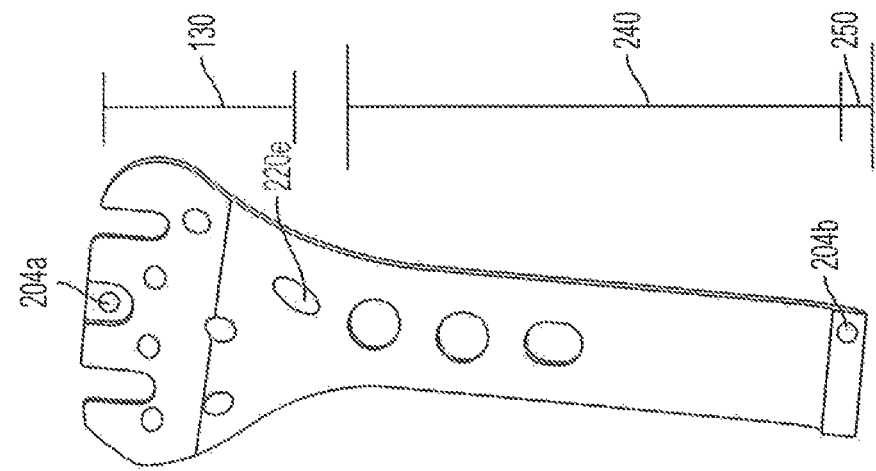
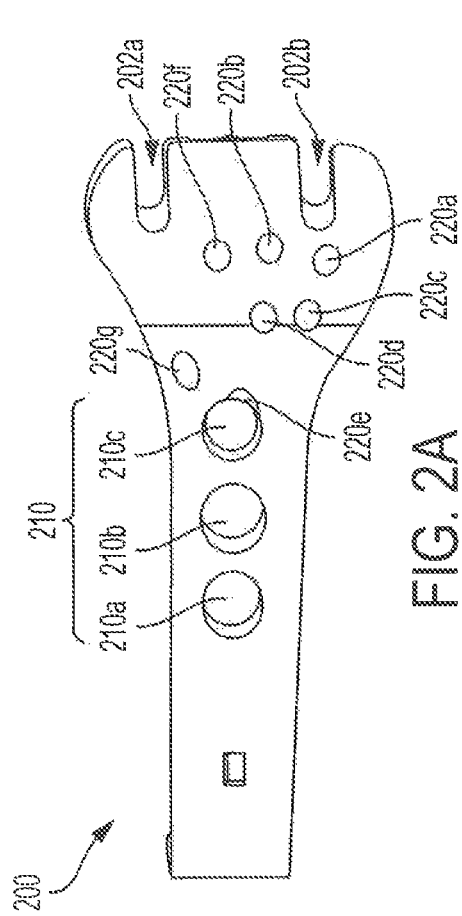
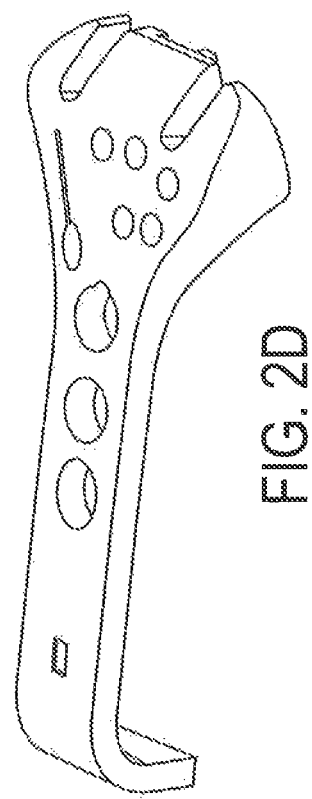
FIG. 2B
FIG. 2A
FIG. 2C
FIG. 2D

WRIST PLATE AND DRILL GUIDE

CROSS-REFERENCE TO RELATED APPLICATION

The present application claims priority to U.S. Provisional Application No. 62/387,231 filed Dec. 23, 2015 and entitled "PRONATOR QUADRATUS SPARING DRILL GUIDE," the disclosure of which is incorporated by reference herein in its entirety.

TECHNICAL FIELD

The present application generally relates to a plate and guide system that provides for fixation of a plate to repair fractured bone, and more particularly to a plate and guide system that enables fixation of a plate to repair a fractured bone with reduced damage to tissue in the vicinity of the fracture.

BACKGROUND

Plates are often used to provide structural integrity to assist with the repair of fractured bone pieces. These plates are typically placed against a surface of the fractured bone, and then screws are used to attach the plate to the pieces of the fractured bone such that the pieces of the fractured bone are arranged in a substantially normal alignment/configuration (e.g., the pieces of the fractured bone are stabilized in positions where the pieces would normally have been before the fracture). It is often the case that tissue (e.g., muscles, etc.) in the vicinity of the bone may be required to be cut to provide access to the bone (e.g., for positioning of the plate against the surface of the bone). For example, and referring to FIG. 10, a diagram illustrating a configuration of bone relative to a muscle is shown. In FIG. 10, various bones of the hand and wrist, a radius bone, and an ulna bone are shown from the volar side. FIG. 10 further illustrates that the pronator quadratus muscle is proximate to the distal end of the radius and ulna bones, and spans portions of both the radius and ulna bones. For fractures of the distal radius bone and/or ulna bone, it is common for the pronator quadratus muscle to be cut to enable a surgeon to place a plate in a desired position along the surface of the distal radius and/or ulna bone prior to inserting screws through the plate to provide fixation for the fractured pieces of the bone.

The cutting of the muscle and other tissue to provide access for placement of the plate may increase the recovery time for the patient, as well as limit the patient's ability to perform actions that require the use of the muscle and/or other tissue that was cut. For example, the pronator quadratus muscle is used to pronate the hand (e.g., turn the hand so that the palm faces downward). If the patient's pronator quadratus muscle is cut to provide access for positioning a plate to provide fixation of a fracture of the distal radius bone, the patient may be unable to, or have limited ability to, pronate his/her hand, and may experience discomfort as well.

BRIEF SUMMARY

The present disclosure describes various embodiments of a plate and guide that enable fixation of a fractured bone while reducing damage to tissue in the vicinity of the fractured bone. The plate may be sized and dimensioned such that the plate may be slid underneath a muscle or other tissue and positioned into a proper location for providing fixation of the plate to the fractured bone without requiring cutting of the muscle or other tissue. The guide may be sized and dimensioned to interface with the plate such that the guide is placed over the top of the muscle or other tissue, thereby enabling the guide to be used for providing screws or other devices (e.g., rods, K-wires, etc.) to the plate in a proper orientation to provide fixation to the fractured bone without requiring cutting of the muscle or other tissue, or reducing the amount of cutting of the muscle.

In an embodiment, a plate is provided and may be configured to provide fixation for fractures of a distal radius bone. The plate may have a shape that is sized and dimensioned to conform to a volar side of a distal radius bone, and the shape may further enable the plate to slide underneath a muscle, such as the pronator quadratus muscle shown in FIG. 10, thereby enabling the plate to be positioned on a volar side of the distal radius bone to provide fixation to treat a fracture of the distal radius bone. The plate may include a plurality of apertures configured to receive various fixation devices, such as screws, K-wires, rods, and the like which are used to fixate the pieces of the fractured radius bone in a desired orientation. In an embodiment, a guide is provided to orient the fixation devices into a proper orientation to provide the desired fixation. In an embodiment, a length of the plate may be configured such that a portion of a proximal end and a portion of a distal end of the plate extend beyond the pronator quadratus muscle, thereby enabling the plate to be removably coupled to the guide without cutting the pronator quadratus muscle. The guide may include a plurality of apertures that may be used to guide the fixation devices through the pronator quadratus muscle and to the corresponding aperture of the plate in a proper orientation/alignment to provide fixation of the pieces of the fractured radius bone. Inserting the fixation devices through the pronator quadratus muscle, as opposed to cutting the quadratus muscle, may reduce the damage caused to the pronator quadratus muscle, and may reduce the recovery time.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding, reference is now made to the following descriptions taken in conjunction with the accompanying drawings, in which:

FIG. 2A is a top view illustrating an embodiment of a guide for providing one or more fixation devices to a plate that is inserted between a bone and tissue;

FIG. 2B is a bottom view illustrating an embodiment of a guide for providing one or more fixation devices to a plate that is inserted between a bone and tissue;

FIG. 2C is a profile view illustrating an embodiment of a guide for providing one or more fixation devices to a plate that is inserted between a bone and tissue;

FIG. 2D is a perspective view illustrating an embodiment of a guide for providing one or more fixation devices to a plate that is inserted between a bone and tissue;

DETAILED DESCRIPTION

Figure 1A:
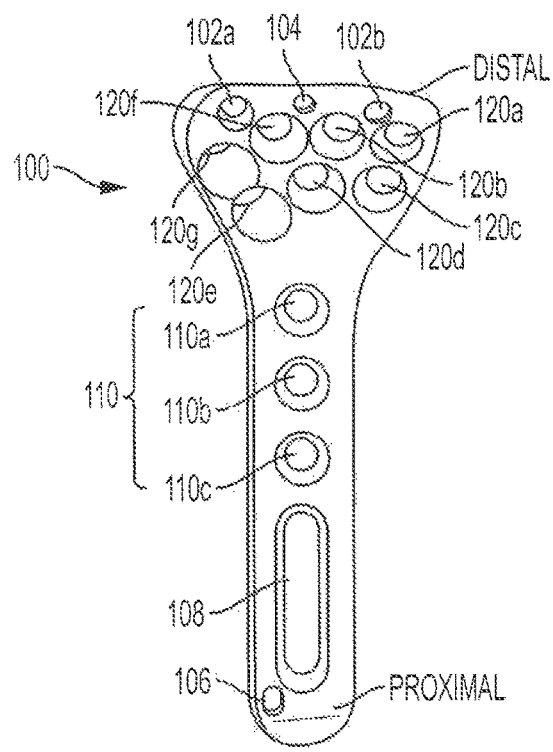
FIG. 1A is a top view illustrating an embodiment of a plate for insertion between a bone and tissue.
Figure 1B:
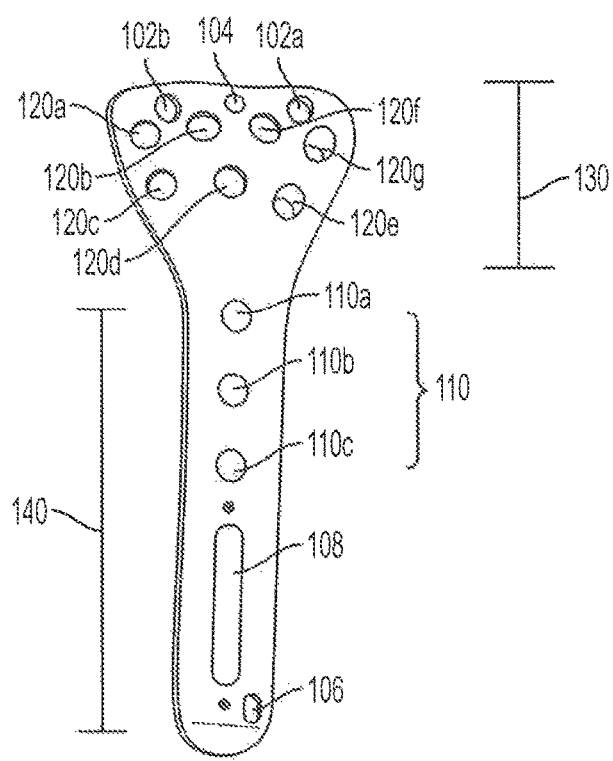
FIG. 1B is a bottom view illustrating an embodiment of a plate for insertion between a bone and tissue.
Figure 1C:
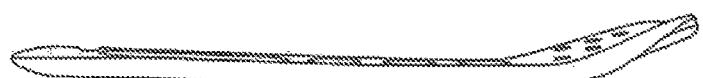
FIG. 1C is a profile view illustrating an embodiment of a plate for insertion between a bone and tissue.
Figure 1D:
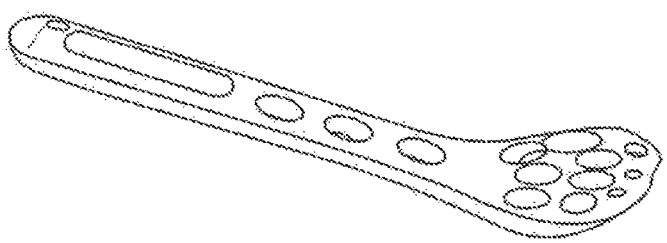
FIG. 1D is a perspective view illustrating an embodiment of a plate for insertion between a bone and tissue.

Referring to FIGS. 1A-1D, various views of an embodiment of a plate for insertion between a bone and tissue are shown as a plate 100, where FIG. 1A is a top view illustrating an embodiment of a plate for insertion between a bone and tissue, FIG. 1B is a bottom view illustrating an embodiment of a plate for insertion between a bone and tissue, FIG. 1C is a profile view illustrating an embodiment of a plate for insertion between a bone and tissue, and FIG. 1D is a perspective view illustrating an embodiment of a plate for insertion between a bone and tissue. As shown in FIGS. 1A-1D, the plate 100 includes a head portion 130 and a shaft portion 140. In an embodiment, the head portion 130 may have a shape that is sized and dimensioned to conform to a portion of a volar side of a radius bone (e.g., a distal head of the radius bone). In additional or alternative embodiments, the head portion 130 may have a shape that is sized and dimensioned to conform to a portion of a head of another bone, or another portion of the head of the radius bone.

The head portion defines a plurality of apertures that may be used in various ways to facilitate fixation of a bone fracture. As shown in FIGS. 1A and 1B, the plurality of apertures may include a first set of apertures 102a, 102b, a second set of apertures 104, 106, a slotted aperture 108, a third set of apertures 110 that includes apertures 110a, 110b, 110c, and a fourth set of apertures 120 that includes apertures 120a, 120b, 120c, 120d, 120e, 120f, 120g. In an embodiment, the first set of apertures may be configured to receive a first type of fixation device (e.g., a rod, a pin, a K-wire, etc.). The first type of fixation device may be designed to be inserted into the apertures 102a, 102b to temporarily hold the plate 100 in a desired orientation while additional fixation devices are provided to other apertures of the plate 100. Once the additional fixation devices have been provided, the fixation devices of the first type may be removed from the plate 100.

The second set of apertures may be configured to interface the plate 100 with a guide (e.g., the guide illustrated in FIGS. 2A-2D). In an embodiment, the second set of apertures may include more than, or less than two apertures. As shown in FIGS. 1A-1D, each aperture of the second set of apertures may be positioned at a proximal or distal end of the plate 100. As explained in more detail below with reference to FIGS. 4A-4D, the plate 100 may be configured to be slid between a bone surface and a muscle or other tissue. By placing the second set of apertures on the proximal or distal ends of the plate 100, the second set of apertures may be positioned such that the guide may be interfaced with the plate 100 without requiring cutting of the muscle or other tissue.

As shown in FIGS. 1A-1D, the shaft portion 140 of the plate 100 includes the slot 108 and the third set of apertures 110. The slot 108 and the third set of apertures 110 may be configured to provide fixation of the plate 100 along a shaft of the bone. Slot 108 may be used as an initial fixation point which allows plate 100 to be fixed in the bone (e.g. in the center of the bone) in a manner that the plate may still be laterally adjusted while the plate is substantially held in place at this initial fixation point. In an embodiment, the slot 108 and the third set of apertures 110 may be configured to provide fixation of the plate 100 along volar side of the shaft of a radius bone. The head portion 130 of the plate 100 includes the fourth set of apertures 120. The fourth set of apertures 120 may be configured to provide various angles for fixation devices to be inserted into the bone to provide fixation of the plate 100 and the pieces of the fractured bone. For example, as explained in more detail below with reference to FIGS. 3A-3G, various ones of the apertures 120a, 120b, 120c, 120d, 120e, 120f, 120g may provide different axial orientations for fixation devices (e.g., bone screws). This may cause the fixation devices to enter the bone at different angles, which may provide for increased fixation.

The plate 100 may be constructed such that it has a thickness that enables the fixation devices to reside within the thickness of the plate 100. For example, when the fixation devices are bone screws, the heads of the bone screws, when screwed into the pieces of the fractured bone, may be housed within thickness plate 100 such that heads of the bone screws do not protrude above the top surface of the plate 100. This may prevent rubbing of the screw heads against the surrounding tissues, which may cause discomfort to the patient, and/or may cause damage to the surrounding tissue. In an embodiment, the apertures may be threaded. In an additional or alternative embodiment, the apertures may be cross-threaded. As the bone screws are screwed into the bone, the cross threading may cause the bone screws to be locked in place, thereby preventing the bone screws from backing out. In an additional or alternative embodiment, the apertures may be formed of a different material that is softer than the material that the bone screws are made of, and, as the bone screws are screwed into the pieces of the fractured bone, the screws may deform the softer material, which may cause the screws to become locked in place and may prevent the bone screws from backing out.

In an embodiment, the plate 100 may be formed using a metal (e.g., titanium). In an additional or alternative embodiment, the plate 100 may be formed using polymers, ceramics, glasses, composite materials, biological materials or tissues, insulators, conductors, semiconductors, other biocompatible or non-biocompatible materials, metals, or a combination thereof. In an embodiment, different materials may be used for individual components. In an additional or alternative embodiment, different materials may be combined in a single component.

Referring to FIGS. 2A-2D, various views of an embodiment of a guide for providing one or more fixation devices to a plate that is inserted between a bone and tissue are shown as a guide 200, where FIG. 2A is a top view illustrating an embodiment of a guide for providing one or more fixation devices to a plate that is inserted between a bone and tissue, FIG. 2B is a bottom view illustrating an embodiment of a guide for providing one or more fixation devices to a plate that is inserted between a bone and tissue, FIG. 2C is a profile view illustrating an embodiment of a guide for providing one or more fixation devices to a plate that is inserted between a bone and tissue, and FIG. 2D is a perspective view illustrating an embodiment of a guide for providing one or more fixation devices to a plate that is inserted between a bone and tissue.

The guide 200 includes a distal end 230, a shaft portion 240, and a proximal end 250. In an embodiment, the distal end 230, the shaft portion 240, and the proximal end 250 may define a space 260. In an embodiment, the space 260 may have a height and length sufficient to span the muscle or tissue that the plate 100 of FIG. 1 has been inserted underneath, and that allows plate interface components 204a, 204b of the guide 200 to be interfaced with the first set of apertures of the plate 100. Accordingly, when the guide 200 is interfaced with the plate 100, the muscle overlying the plate 100 may be located within the space 160. Stated another way, the guide 200 may be placed over the top of the muscle, and interfaced with portions of the plate 100 that extend beyond the muscle overlying the plate 100, thereby enabling the guide 200 and the plate 100 to be utilized for providing fixation of a bone fracture without requiring that the muscle be cut. In an embodiment, the muscle may be the pronator quadratus muscle, and the guide 200 may be configured to be placed over the pronator quadratus muscle. In such a configuration, the guide 200 may be interfaced with a plate (e.g., the plate 100 of FIG. 1) that has been slid underneath the pronator quadratus muscle and positioned such that the distal and proximal ends of the plate extend beyond the pronator quadratus to enable the guide 200 to be interfaced with the plate. In an embodiment, the plate interface components 204a, 204b may be removably coupled with the first set of apertures of the plate 100 via a compression fit, snap fit, and the like. In an additional or alternative embodiment, the components 204a, 204b may be pins that fit within the first set of apertures. Any means of connecting plate 100 with guide 200 may be utilized which allows for guide 200 to be placed such that the orientation of the respective guide holes is aligned with respect to the underlying apertures of plate 100. In some aspects, the plate and guide may have ridges that nest with each other when joined. Further, the guide 200 may include proximal and distal edges that overlap the proximal and distal edges of the plate in a snug fashion in order to keep proper alignment. Further, it is noted that the illustrated embodiment contains interface components 204a and 204b which are on opposite ends of guide 200. Fixation of the guide at two points may be desired in order to prevent translational movement between plate 100 and guide 200 which would cause the slots of guide 200 and apertures of plate 100 to misalign. In some aspects a third and/or fourth interface components may be provided.

In an embodiment, the guide 200 may include one or more slots. For example, in FIGS. 2A-2D a first slot 202a and a second slot 202b are shown. The slots may be configured to orient fixation devices of the first fixation device type (e.g., rods, pins, K-wires, and the like) such that they are received in proper alignment with the first set of apertures of the plate 100. The slots 202a, 202b enable the guide to be removed one the desired fixation devices have been provided, as described in more detail below, and then, with the guide 200 removed, the K-wires, rods, or pins may be removed or cut flush with the top of the plate.

The guide 200 may be used to pre-drill holes in the appropriate places on the bone such that bone screws may be used to fixate the plate 100 to the bone. For example, a surgeon may use the guide 200 to pre-drill holes for one or more bone screws. Once the holes are pre-drilled, the surgeon may insert a K-wire into each of the pre-drilled holes using the guide 200, and, once all holes have been pre-drilled and the K-wires have been inserted, the guide 200 may be removed. Guided by the K-wires that were inserted into the pre-drilled holes, the surgeon may then use cannulated screws to fixate the plate 100 to the bone.

In addition to the one or more slots, the guide 200 may define a plurality of apertures that are configured to orient fixation devices to the appropriate apertures of the plate 100 to provide fixation of a bone fracture. For example, the aperture 210a may be configured to orient a fixation device in proper alignment with the aperture 110a of the plate 100, the aperture 210b may be configured to orient a fixation device in proper alignment with the aperture 110b, the aperture 210c may be configured to orient a fixation device in proper alignment with the aperture 110c, the aperture 220a may be configured to orient a fixation device in proper alignment with the aperture 120a, the aperture 220b may be configured to orient a fixation device in proper alignment with the aperture 120b, the aperture 220c may be configured to orient a fixation device in proper alignment with the aperture 120c, the aperture 220d may be configured to orient a fixation device in proper alignment with the aperture 120d, the aperture 220e may be configured to orient a fixation device in proper alignment with the aperture 120e, the aperture 220f may be configured to orient a fixation device in proper alignment with the aperture 120f, and the aperture 220g may be configured to orient a fixation device in proper alignment with the aperture 120g. Thus, the guide 200 may enable a surgeon to provide the fixation devices to the appropriate one of the apertures on the plate 100 to provide a desired fixation despite one or more of the apertures of the plate 100 being hidden beneath the muscle. As the fixation devices are provided, they may be passed through the muscle overlying the plate 100. This may cause minor damage to the muscle, but such damage may be trivial in terms of recovery time compared to cutting the muscle.

In an embodiment, one or more of the guide apertures may be within or reside in another one of the guide apertures. For example, as shown in FIG. 2A, the guide aperture 220e is at least partially within the guide aperture 210c. This may enable the guide apertures to provide different angles which may not otherwise be possible, and may enable different angles of fixation which may be better suited for certain types/locations of fractures. In an additional or alternative embodiment, a fixation system may provide two or more guides, each providing at least one different angle relative to other guides of the fixation system. This may enable selection of a guide that provides the appropriate angles for fixation of a complex fracture. Further, because the guide is removably coupled to the plate, a first set of holes may be pre-drilled using a first guide, and a second set of one or more holes may be pre-drilled using a second guide, where the second guide provides at least angle for providing fixation that is not provided by the first guide. It is noted that if multiple guides are used, screws may be driven into the bone prior to use of the next guide. Additionally, it is noted that in embodiments providing multiple guides, a first guide may be used to pre-drill holes, while a second guide may be used to insert bone screws. For example, the first guide may have smaller holes relative to the second guide, where the larger holes of the second guide are configured to accommodate the larger size of the bone screw and allow the bone screw to pass through the guide when being drilled into the bone. Using multiple guides in this fashion may simplify the process of providing the bone screw through the muscle to the appropriate hole in the plate (e.g., because the holes in the second guide may provide the screw to the bone at the same angle and orientation as the corresponding hole pre-drilled using the first guide), which may reduce the damage to the tissue of the muscle (e.g., relative to damage caused to the surrounding tissue when the surgeon has to fish the screw through the muscle manually to locate the appropriate pre-drilled hole) and thereby improve the recovery time even further.

The guide 200 may be constructed such that it has a thickness that enables the fixation devices to be maintained in a proper orientation as the fixation devices pass through the muscle and the plate 100 into the bone. In an embodiment, the guide 200 may be formed using a metal (e.g., titanium). In an additional or alternative embodiment, the guide 200 may be formed using polymers, ceramics, glasses, composite materials, biological materials or tissues, insulators, conductors, semiconductors, other biocompatible or non-biocompatible materials, metals, or a combination thereof. In an embodiment, different materials may be used for individual components. In an additional or alternative embodiment, different materials may be combined in a single component.

Figure 3A:
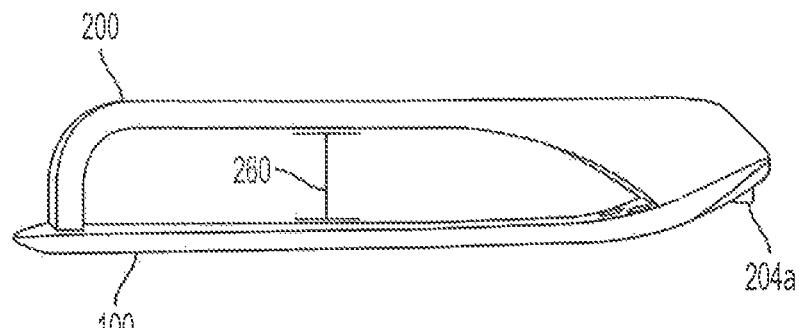
FIG. 3A is a profile view illustrating an embodiment of system including a guide and plate for repairing a bone fracture with reduced damage to tissue in the vicinity of the bone fracture.
Figure 3B:
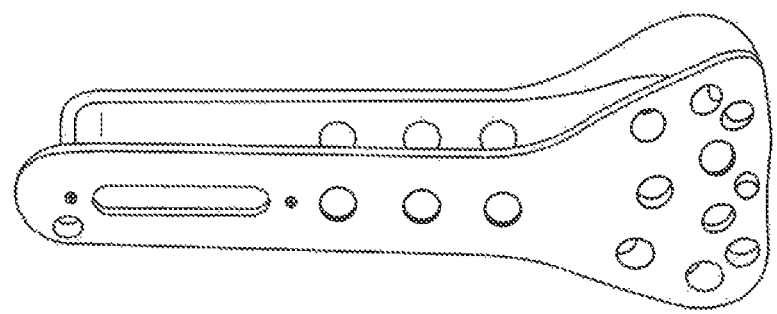
FIG. 3B is a perspective view illustrating an embodiment of system including a guide and plate for repairing a bone fracture with reduced damage to tissue in the vicinity of the bone fracture.
Figure 3C:
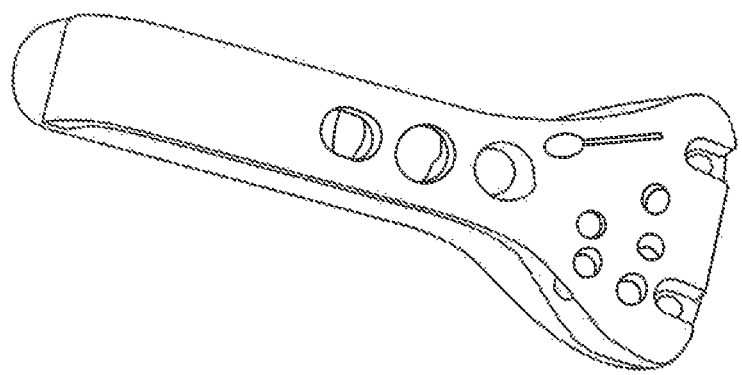
FIG. 3C is another perspective view illustrating an embodiment of system including a guide and plate for repairing a bone fracture with reduced damage to tissue in the vicinity of the bone fracture.
Figure 3D:
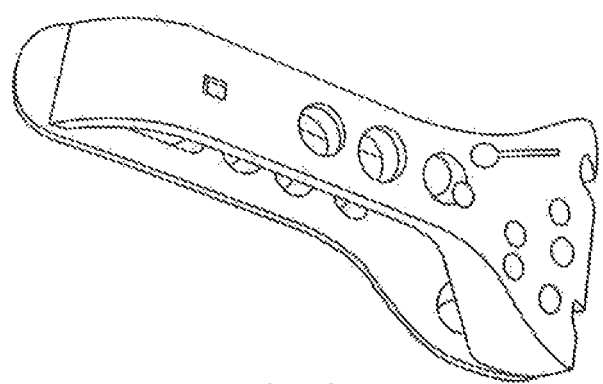
FIG. 3D is another perspective view illustrating an embodiment of system including a guide and plate for repairing a bone fracture with reduced damage to tissue in the vicinity of the bone fracture.
Figure 3F:
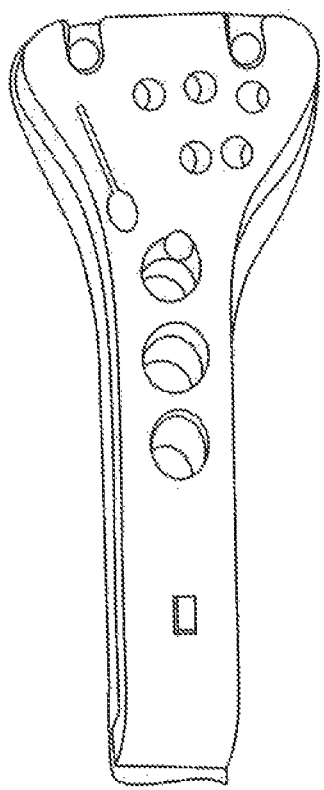
FIG. 3F is a top view illustrating an embodiment of system including a guide and plate for repairing a bone fracture with reduced damage to tissue in the vicinity of the bone fracture.
Figure 3E:
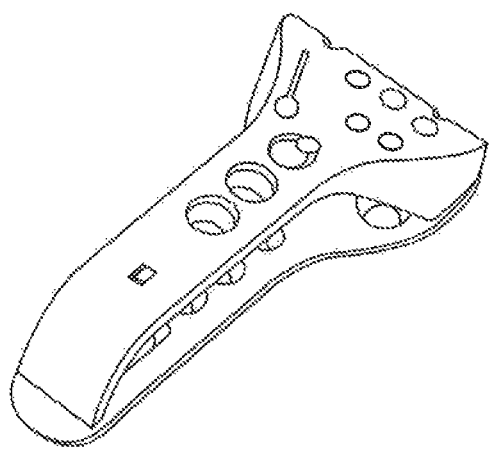
FIG. 3E is another perspective view illustrating an embodiment of system including a guide and plate for repairing a bone fracture with reduced damage to tissue in the vicinity of the bone fracture.
Figure 3G:
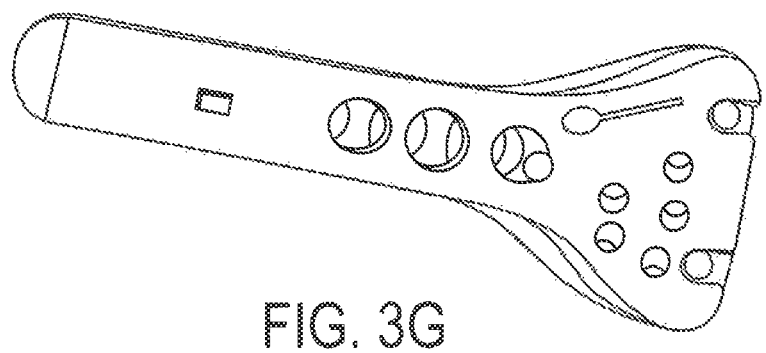
FIG. 3G is another perspective view illustrating an embodiment of system including a guide and plate for repairing a bone fracture with reduced damage to tissue in the vicinity of the bone fracture.

Referring to FIGS. 3A-3G, various views illustrating aspects of an embodiment of a system including a guide and plate for repairing a bone fracture with reduced damage to tissue in the vicinity of the bone fracture, where FIG. 3A illustrates a profile view of an embodiment of system including a guide and plate for repairing a bone fracture with reduced damage to tissue in the vicinity of the bone fracture, FIG. 3B illustrates a perspective view of an embodiment of system including a guide and plate for repairing a bone fracture with reduced damage to tissue in the vicinity of the bone fracture, FIG. 3C illustrates another perspective view of an embodiment of system including a guide and plate for repairing a bone fracture with reduced damage to tissue in the vicinity of the bone fracture, FIG. 3D illustrates another perspective view of an embodiment of system including a guide and plate for repairing a bone fracture with reduced damage to tissue in the vicinity of the bone fracture, FIG. 3E illustrates a profile view of an embodiment of system including a guide and plate for repairing a bone fracture with reduced damage to tissue in the vicinity of the bone fracture, FIG. 3F illustrates a top view of an embodiment of system including a guide and plate for repairing a bone fracture with reduced damage to tissue in the vicinity of the bone fracture, and FIG. 3G illustrates another perspective view of an embodiment of system including a guide and plate for repairing a bone fracture with reduced damage to tissue in the vicinity of the bone fracture.

In FIG. 3A the plate 100 and the guide 200 are shown in an interfaced arrangement, and the space 260 can be seen. When the plate 100 is fixed to a bone, a muscle may fill at least a portion of the space 260 formed between the plate 100 and the guide 200. For example, when the plate 100 is configured for use repairing fractures of the distal radius bone, at least a portion of the space 260 may be filled by the pronator quadratus muscle. In an embodiment, the distal end 230 of the guide 200 may interface with the head portion of the plate 100 at an angle, as shown in FIG. 3A. In an additional or alternative embodiment, the distal end 230 of the guide 200 may interface with the head portion of the plate 100 perpendicularly, or at a steeper, or more shallow angle depending on the particular location and bone for which the plate 100 is being used.

FIG. 3C illustrates that the guide aperture 220d aligns with the aperture 120d of the plate 100, and has a different axial orientation than the remaining guide apertures. Thus, a fixation device provided based on a pre-drilled hole and K-wire facilitated by the guide aperture 220d may travel through the muscle and into the aperture 120d of the plate 100 at an angle that is unique relative to the angles of insertion for other fixation devices. FIG. 3D illustrates that the guide aperture 220e may be located at least partially within the guide aperture 210e. This may enable a fixation device (e.g., a bone screw) to be inserted at a shallower angle than other fixation devices provided based on a pre-drilled hole and K-wire facilitated by other apertures of the guide 200, which may be useful for providing fixation for certain types of fractures/bone fragments. FIG. 3E illustrates that the guide aperture 220g aligns with the aperture 120g of the plate 100, and has a different axial orientation than the remaining guide apertures. Thus, a fixation device provided based on a pre-drilled hole and K-wire facilitated by the guide aperture 220g may travel through the muscle and into the aperture 120g of the plate 100 at an angle that is unique relative to the angles of insertion for other fixation devices. FIG. 3F illustrates that the guide aperture 220c aligns with the aperture 120c of the plate 100. In an embodiment, a fixation device provided based on a pre-drilled hole and K-wire facilitated by the guide aperture 220c and the aperture 120c may have a different axial orientation than the remaining guide apertures. Thus, a fixation device provided based on a pre-drilled hole and K-wire facilitated by the guide aperture 220c may travel through the muscle and into the aperture 120c of the plate 100 at an angle that is unique relative to the angles of insertion for other fixation devices. FIG. 3G illustrates that the guide aperture 220b aligns with the aperture 120b of the plate 100, and has a different axial orientation than the remaining guide apertures. Thus, a fixation device provided based on a pre-drilled hole and K-wire facilitated by the guide aperture 220b may travel through the muscle and into the aperture 120b of the plate 100 at an angle that is unique relative to the angles of insertion for other fixation devices.

Figure 4A:
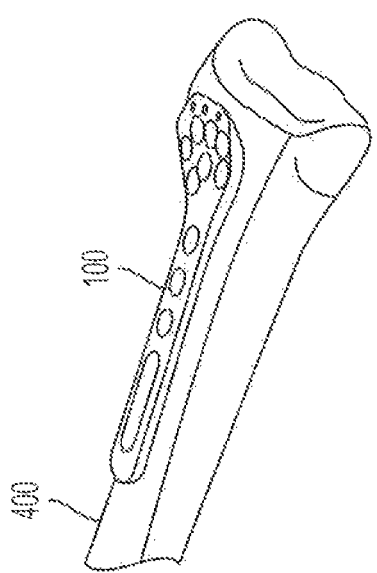
FIG. 4A is a perspective view illustrating an embodiment of positioning a plate into alignment for repairing a bone fracture with reduced damage to tissue in the vicinity of the bone fracture.

Referring to FIG. 4A, a perspective view illustrating an embodiment of positioning a plate into alignment for providing fixation of a plate to a fractured bone with reduced damage to tissue in the vicinity of the bone fracture is shown. As shown in FIG. 4A, the plate 100 may be positioned adjacent a surface of a bone 400. In an embodiment, the plate 100 may be positioned adjacent the surface of the bone 400 by sliding at least a portion of the plate 100 underneath a muscle. In an embodiment, the bone 400 may be the radius bone, and the plate 100 may be positioned adjacent distal surface of the radius bone on the volar side by sliding the plate 100 underneath the pronator quadratus muscle.

Figure 4B:
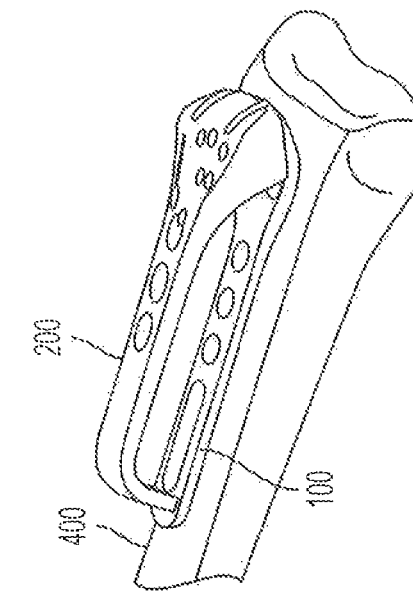
FIG. 4B is a perspective view illustrating an embodiment of positioning a guide to interface with a plate that has been positioned in alignment to provide fixation of a plate to a fractured bone with reduced damage to tissue in the vicinity of the bone.

Referring to FIG. 4B, a perspective view illustrating an embodiment of positioning a guide to interface with a plate that has been positioned in alignment to provide fixation of a plate to a fractured bone with reduced damage to tissue in the vicinity of the bone fracture is shown. As shown in FIG. 4B, the guide 200 may be interfaced with the plate 100 (e.g., using the guide interface components and apertures of the plate 100, such as the apertures 104, 106). In an embodiment, when the guide 200 is interfaced with the plate 100, the guide 200 may be placed over a muscle, and the muscle may reside in the space between the guide 200 and the plate 100. In an embodiment, the guide 200 may be placed over the top of a pronator quadratus muscle.

Figure 4C:
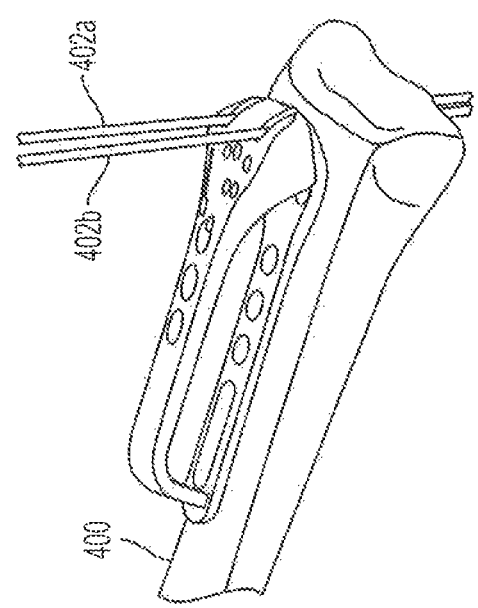
FIG. 4C is another perspective view illustrating an embodiment of providing fixation devices to a plate using a guide.

Referring to FIG. 4C, another perspective view illustrating an embodiment of providing fixation devices to a plate using a guide is shown. As shown in FIG. 4C, K-wires 402a, 402b (or another type of fixation device) may be inserted through the slots of the guide 200 and into the apertures 102a, 102b of plate 100. Once the K-wires 402a, 402b have been provided, the surgeon may pre-drill holes for one or more bone screws using particular ones of the guide apertures. It is noted that holes for K-wires and bone screws may be pre-drilled using different size drill bits, resulting in different sizes of pre-drilled holes being present in the bone (e.g., smaller holes for K-wires and larger holes for bone screws). Once all holes have been pre-drilled and the K-wires have been inserted into select ones of the pre-drilled holes, such as holes corresponding to the first set of apertures 102a, 102b, the guide 200 may be removed.

Figure 4D:
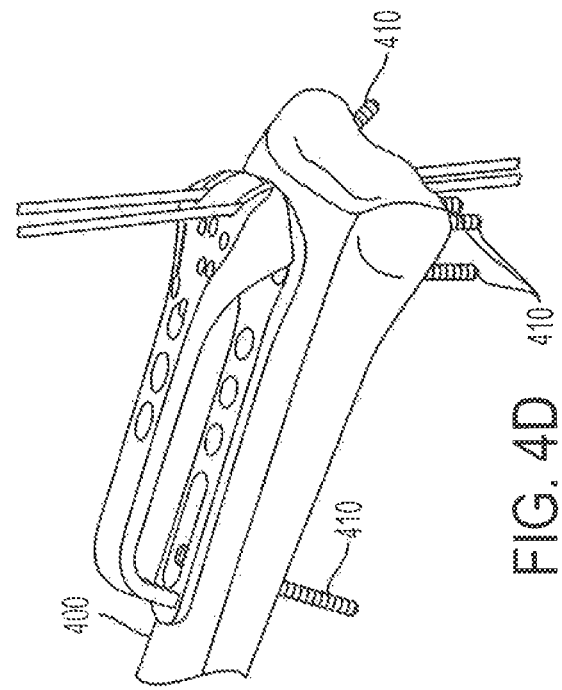
FIG. 4D is another perspective view illustrating an embodiment of providing additional fixation devices to a plate using a guide.

Referring to FIG. 4D, another perspective view illustrating an embodiment of providing additional fixation devices to a plate using a guide. As shown in FIG. 4D, fixation devices, such as bone screws, may be provided to the corresponding apertures of the plate 100 to provide fixation of the plate 100 to the fractured bone 400. In an embodiment, the fixation devices may include cannulated screws that are guided by K-wires that have been inserted into the pre-drilled holes. In embodiments where one or more cannulated screws are utilized, a cannulated drill may be used, with or without the guide 200, to pre-drill holes to receive the cannulated screws, and one or more of the K-wires may be used to guide the screws to the one or more pre-drilled holes, then the K-wires may be removed. In embodiments where cannulated screws are provided, the cannulated drill may utilize the K-wires as guides to pre-drill the holes prior to providing the cannulated screws. Once, the bone screws have been provided, the K-wires may be removed. In embodiments where cannulated screws are not utilized, the K-wires may be inserted to select ones of the pre-drilled holes to maintain an orientation of the plate 100, and then bone screws may be inserted through the muscle and screwed into the bone after removal of the guide 200. In an embodiment, the locations of the K-wires may be configured to provide reference points for the locations of the pre-drilled holes that are to receive screws. For example, K-wires inserted into the aperture 102a may serve as a reference point for providing screws to apertures 120f and 120g, which are just below and to either side of the aperture 120a. As the fixation devices are provided, they may travel through the muscle positioned between the plate 100 and the guide 200. Although inserting the screws and other fixation devices through the muscle may cause minor damage to the muscle, the recovery time for such damage is significantly less than the recovery time required when the muscle is cut. Thus, the plate 100 and the guide 200 provide fixation for a bone fracture with a reduced impact to tissue and muscle surrounding the fractured portion of the bone, and may result in a faster recovery time for any damage to the tissue and muscle surrounding the fractured portion of the bone.

Figure 5:
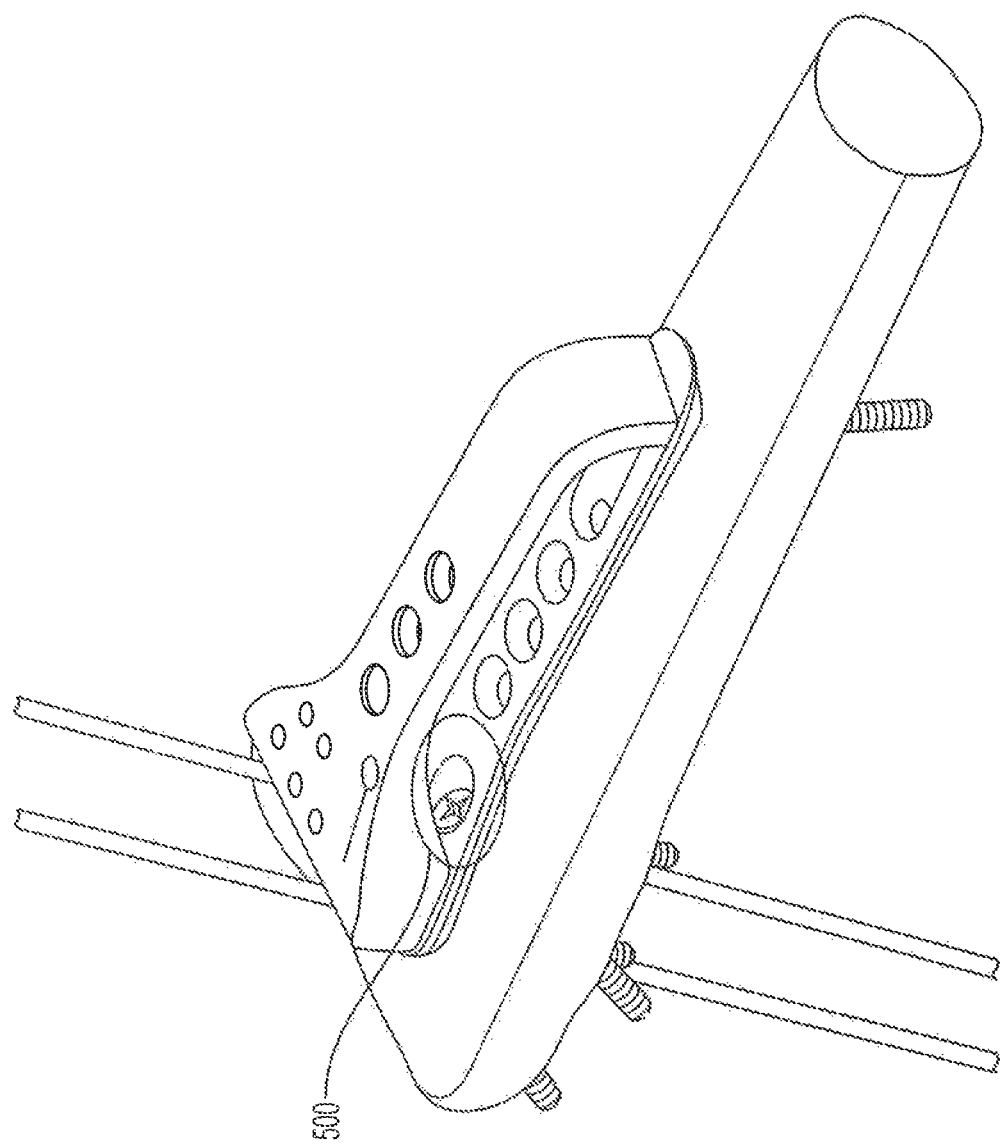
FIG. 5 is a perspective view of an embodiment of a system for providing fixation of a plate to a fractured bone according to embodiments of the present disclosure.
Figure 6:
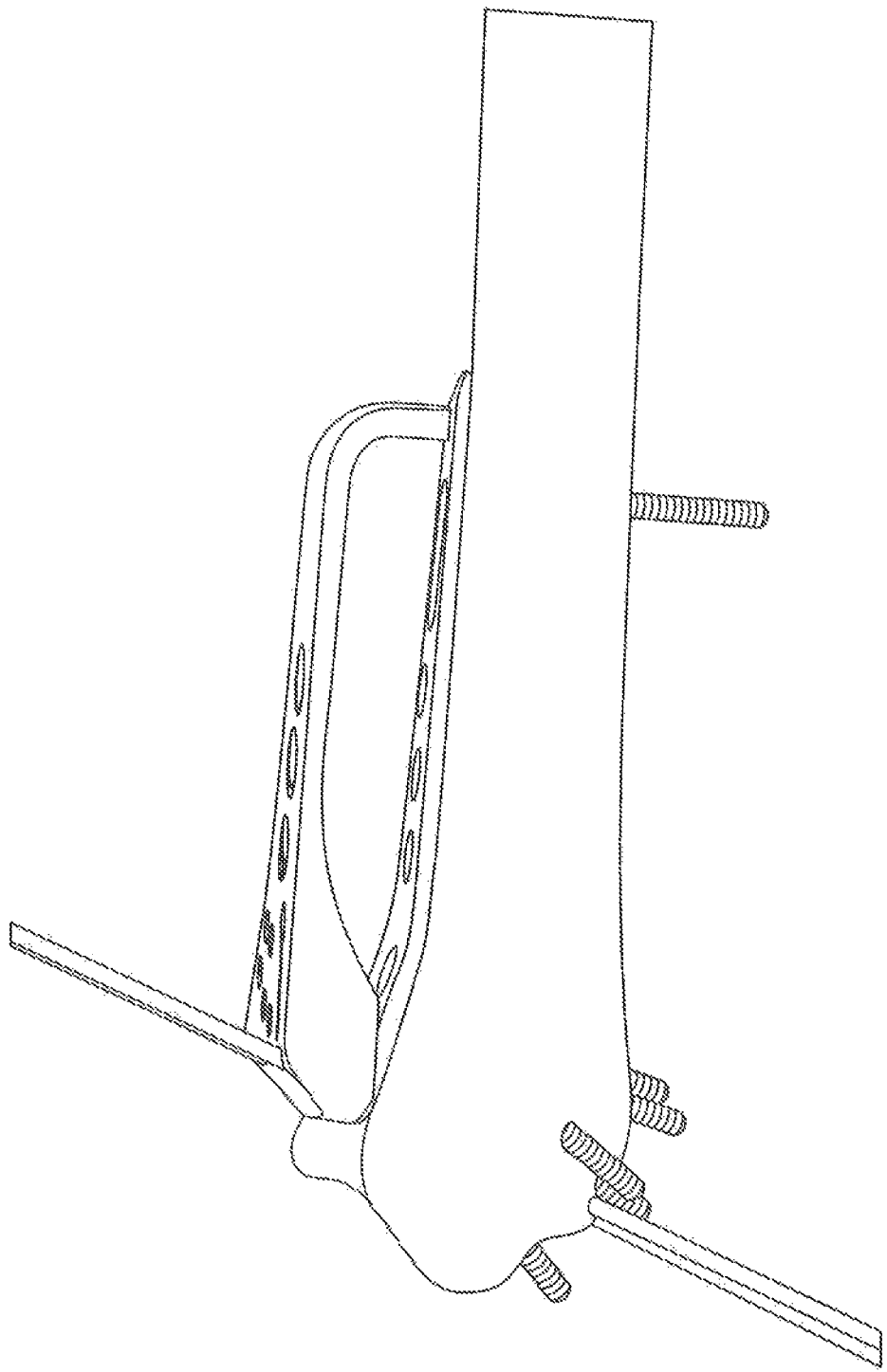
FIG. 6 is a side view of an embodiment of a system for providing fixation of a plate to a fractured bone according to embodiments of the present disclosure.
Figure 7:
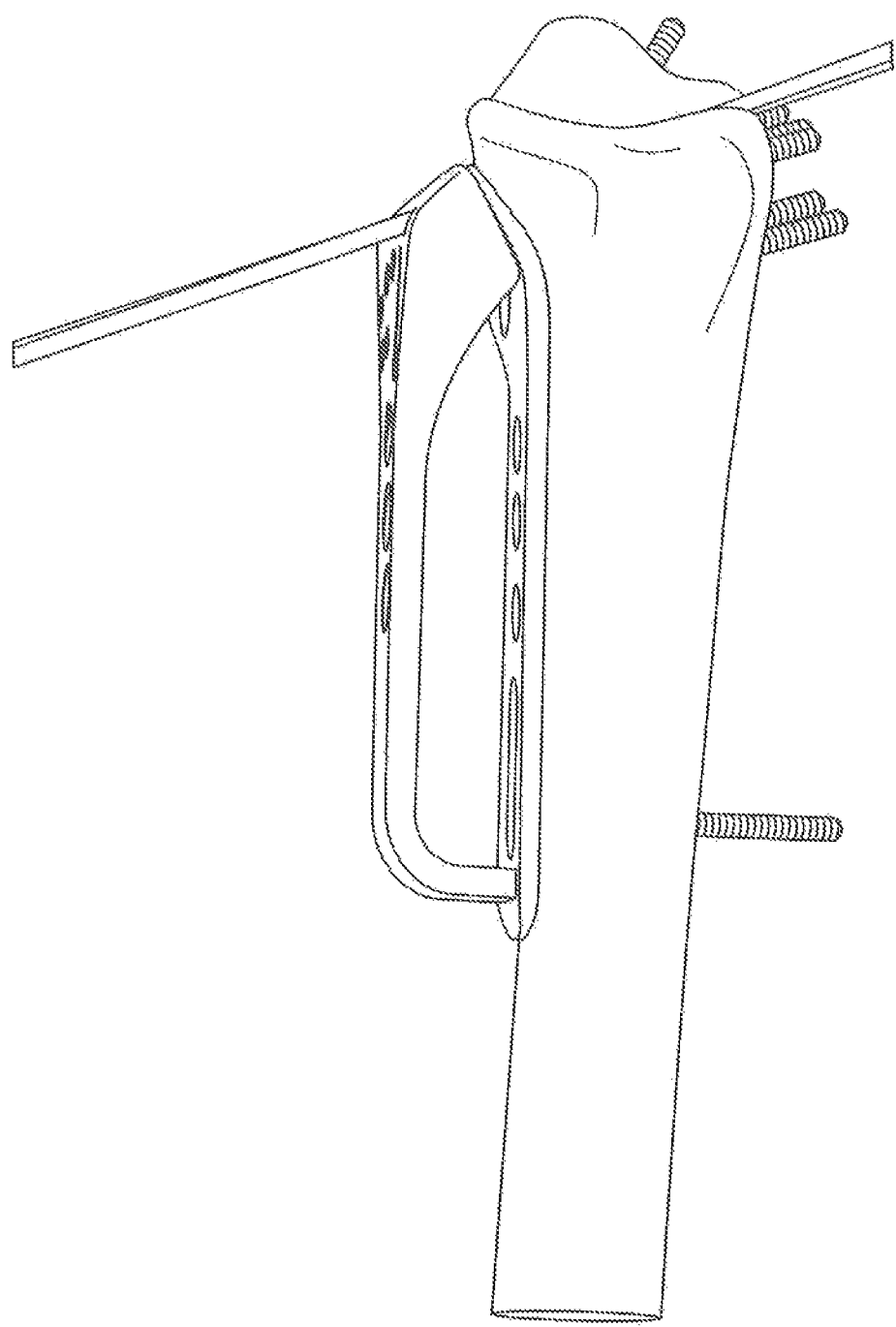
FIG. 7 is another side view of an embodiment of a system for providing fixation of a plate to a fractured bone according to embodiments of the present disclosure.
Figure 8:
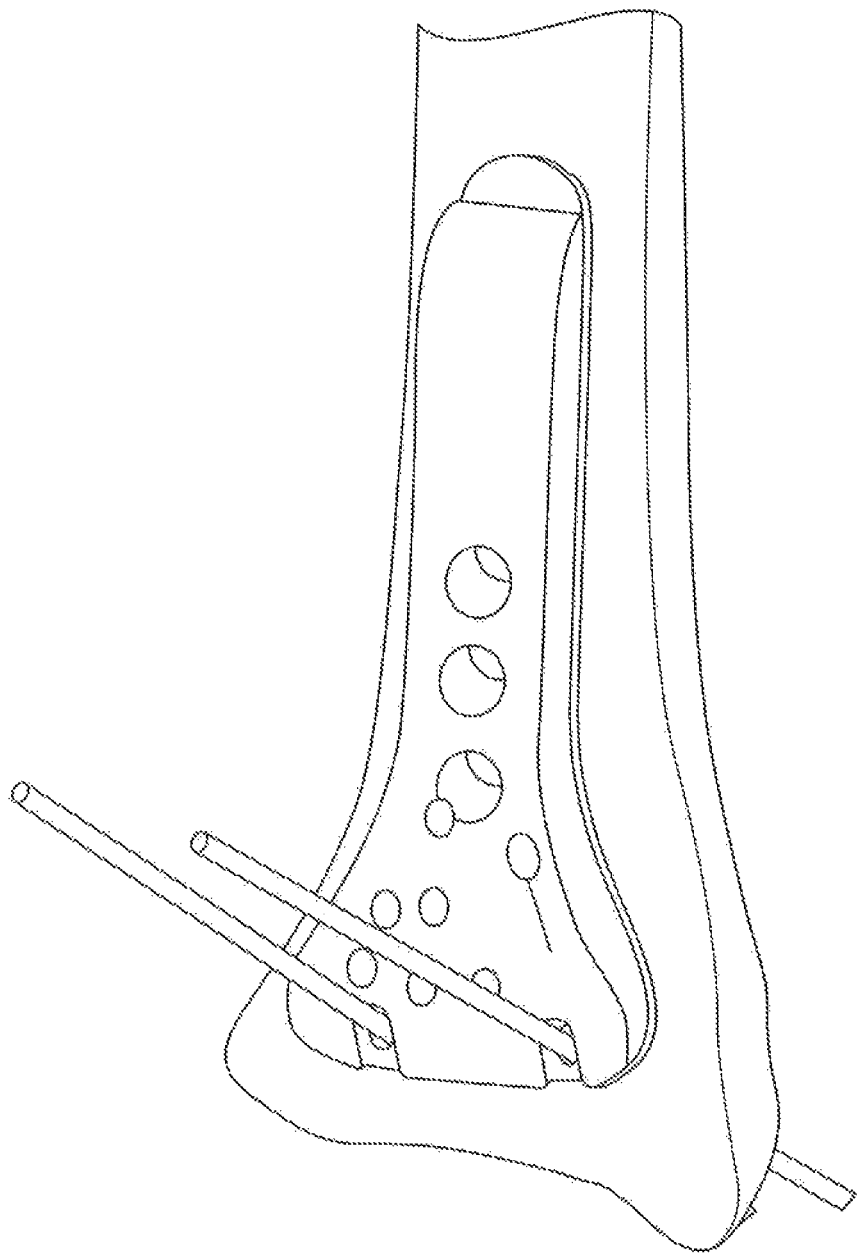
FIG. 8 is a top view of an embodiment of a system for providing fixation of a plate to a fractured bone according to embodiments of the present disclosure.
Figure 9:
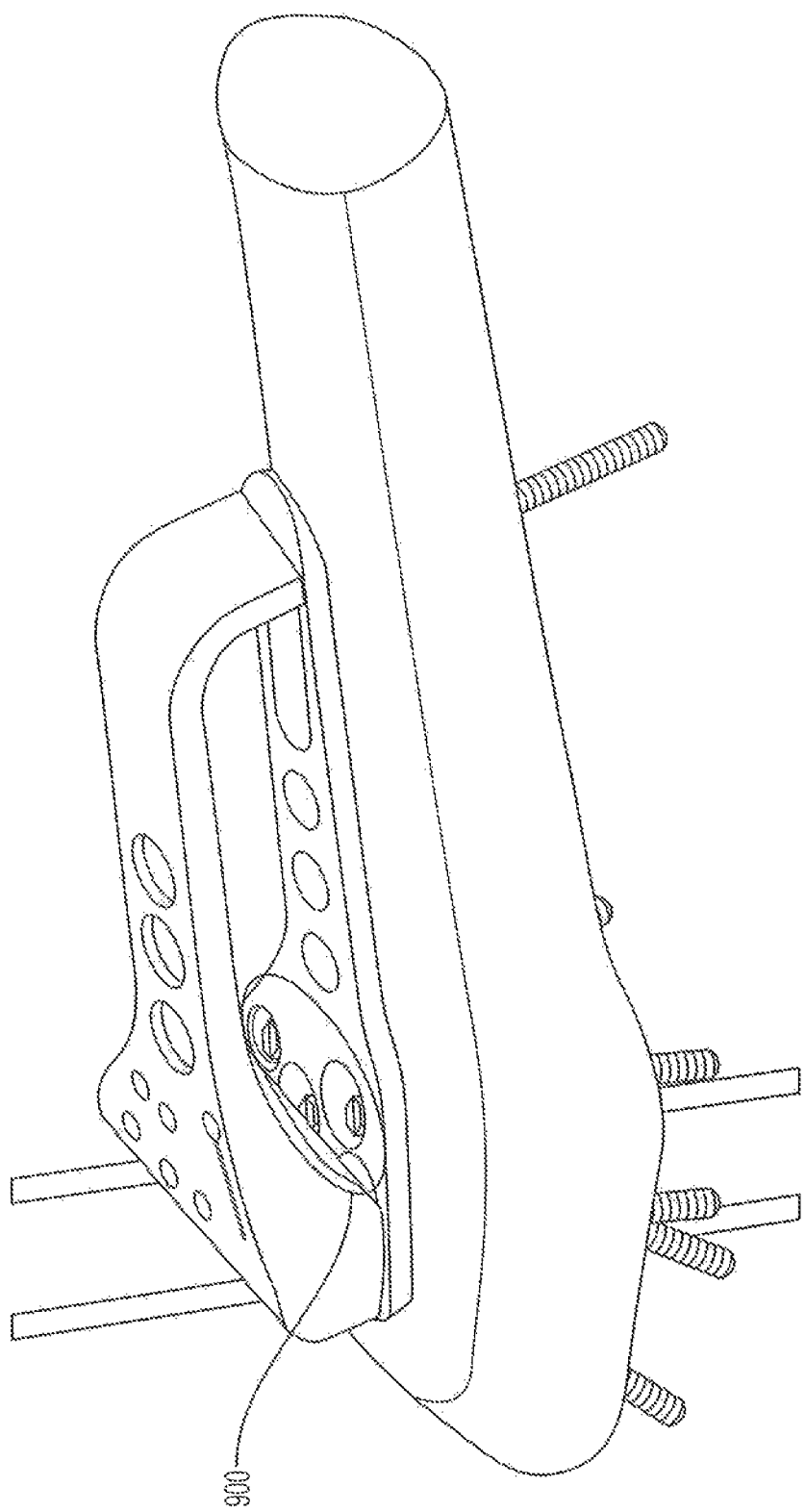
FIG. 9 is another perspective view of an embodiment of a system for providing fixation of a plate to a fractured bone according to embodiments of the present disclosure.
Figure 10:
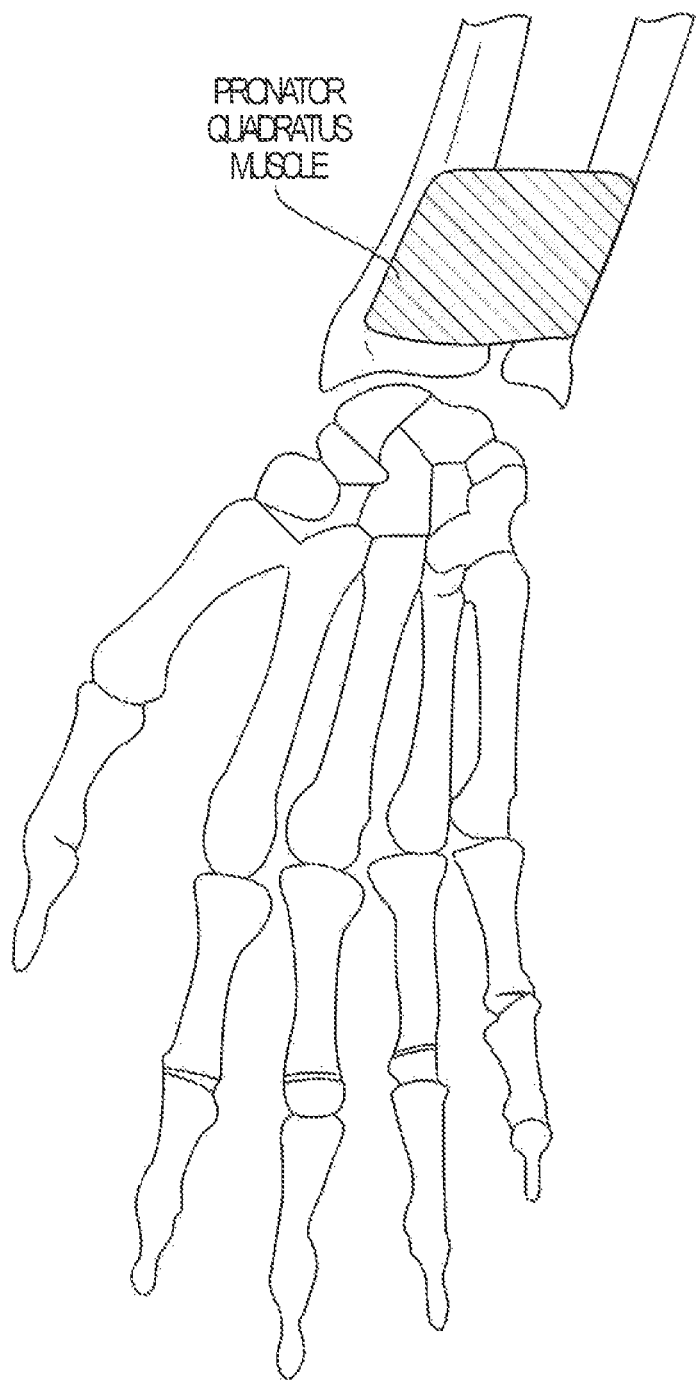
FIG. 10 is a diagram illustrating a configuration of bone relative to a muscle.

FIGS. 5-9 illustrate various views and aspects of an embodiment of positioning a plate into alignment for repairing a bone fracture with reduced damage to tissue in the vicinity of the bone fracture. As shown in FIG. 5 at 500, and as shown in FIG. 9, at 900, the heads of the bone screws may be seated within, and below a top surface of, the plate 100. This may prevent the heads of the bone screws from rubbing muscle and other tissues adjacent to the plate 100.

Figure 11:
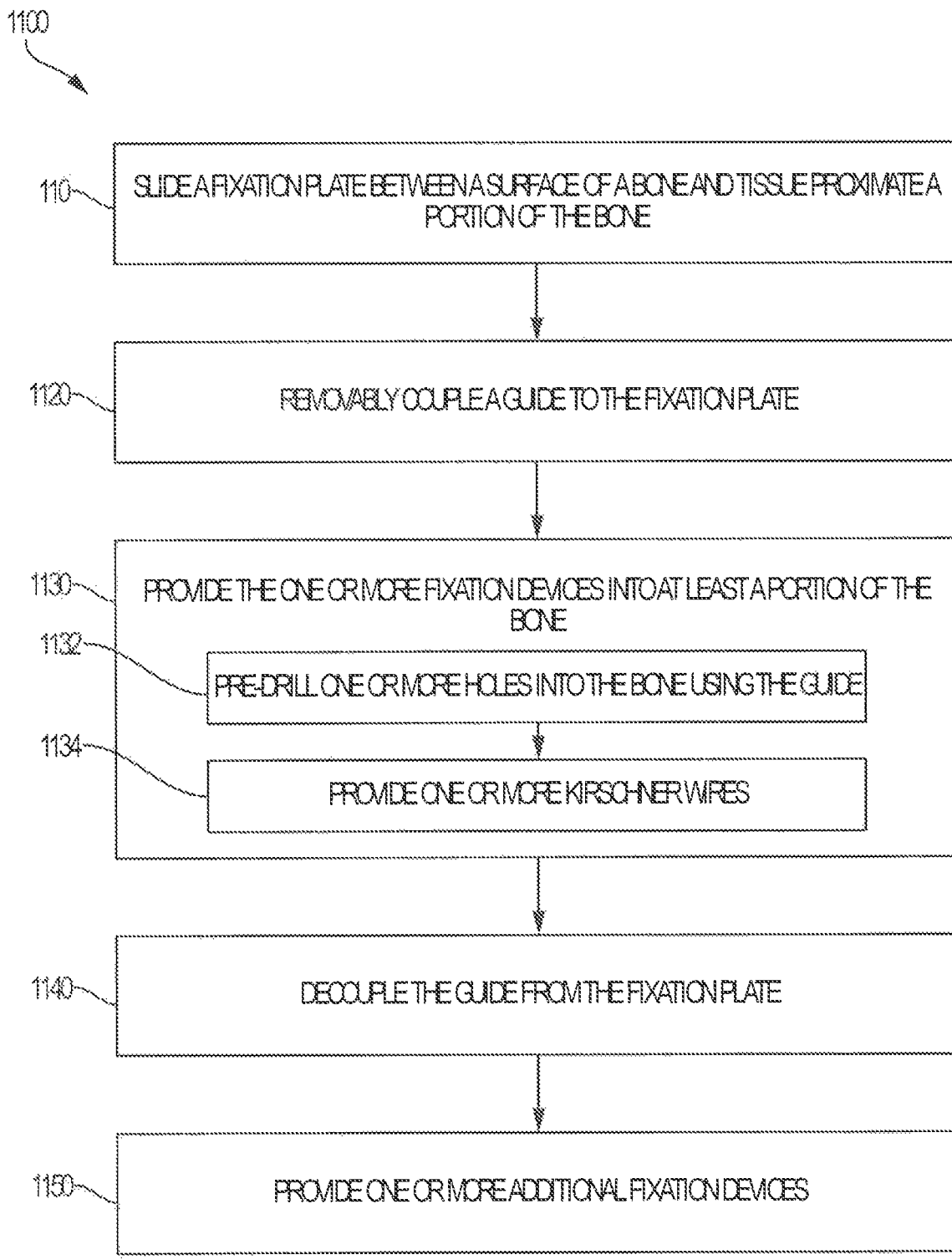
FIG. 11 is a flow diagram of a method for providing fixation of a fracture of a bone using a bone fixation system configured to reduce damage to tissue proximate a portion of the bone during the providing of the fixation in accordance with embodiments.

Referring to FIG. 11, a flow diagram of a method for providing fixation of a fracture of a bone using a bone fixation system configured to reduce damage to tissue proximate a portion of the bone during the providing of the fixation in accordance with embodiments is shown as a method 1100. In an embodiment, the bone fixation system may comprise the bone fixation plate 100 of FIGS. 1A-1D and 3A-9, and the guide 200 of FIGS. 2A-2D, 3A-3G, 4B-9. In an embodiment, the method 1100 may be performed to provide fixation of a fracture of a radius bone, and the tissue may correspond to a pronator quadratus muscle.

Figure 12A:
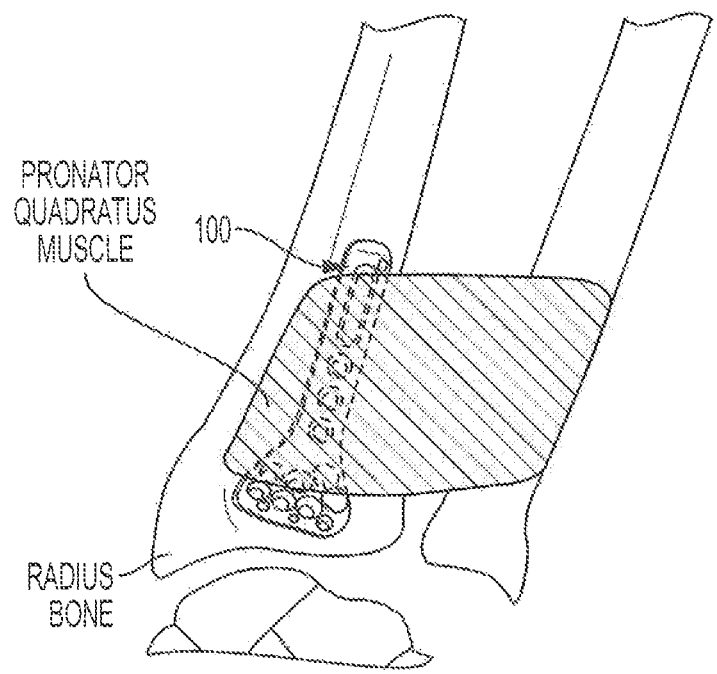
FIG. 12A is a diagram illustrating aspects relating to positioning of a fixation plate in accordance with embodiments.

At 1110, the method 1100 includes sliding a fixation plate between a surface of the bone and the tissue. The fixation plate comprises a head portion, a shaft portion, and a plurality of openings configured to receive one or more fixation devices. In an embodiment, the head portion of the fixation plate may correspond to the head portion 130 of plate 100, the shaft portion of the fixation plate may correspond to the shaft portion 140 of plate 100, and the plurality of openings may include one or more of the first set of apertures, the second set of apertures, the slotted aperture, the third set of apertures that includes apertures, and the fourth set of apertures described above with respect to plate 100. When the fixation plate is slid between the surface of the bone and the tissue, at least a part of the head portion and a part of shaft portion of the fixation plate extend beyond the tissue, as shown in FIG. 12A.

Figure 12B:
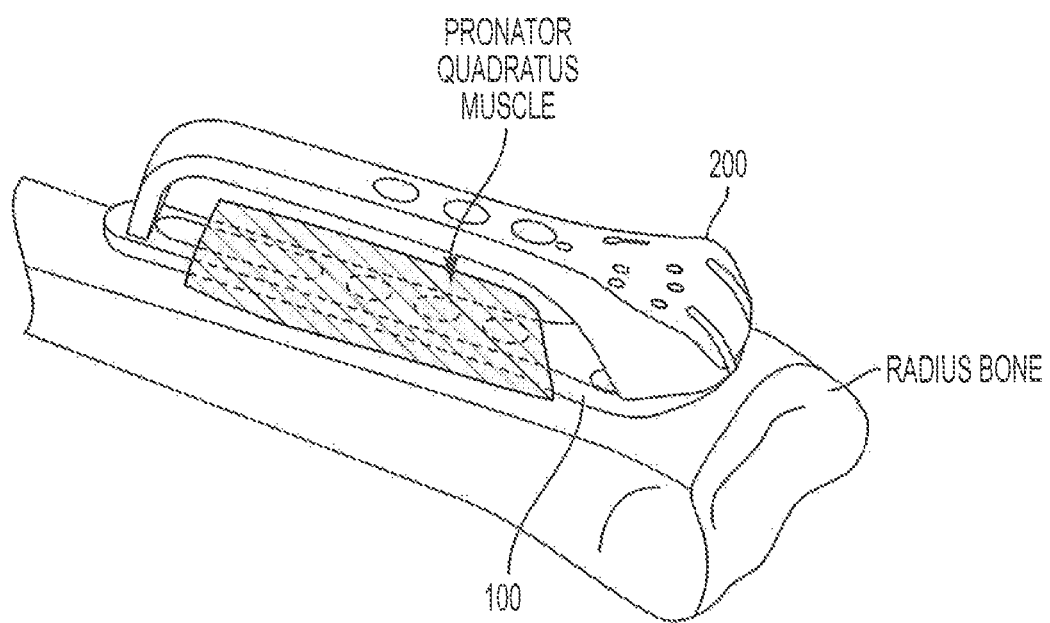
FIG. 12B is a diagram illustrating aspects of a fixation system comprising a fixation plate and guide configured in accordance with embodiments.

At 1120, the method 1100 includes removably coupling a guide to the fixation plate. The guide comprises a distal end portion, a shaft portion, a proximal end portion, and a plurality of guide openings. In an embodiment, the distal end portion may correspond to the distal end 230 of the guide 200 of FIGS. 2A-2D, 3A-3G, 4B-9, the shaft portion may correspond to the shaft portion 240 of the guide 200 of FIGS. 2A-2D, 3A-3G, 4B-9, the proximal end portion may correspond to the proximal end 250 of the guide 200 of FIGS. 2A-2D, 3A-3G, 4B-9, and the plurality of guide openings may correspond to the slots of the guide 200, the plurality of apertures of the guide 200, or a combination thereof. The guide may be removably coupled to the fixation plate at the part of the head portion and the part of the shaft portion that extend beyond the tissue, and, when the guide is removably coupled to the fixation plate, the tissue is disposed in a space between the fixation plate and the distal end portion, the shaft portion, and the proximal end portion of the guide, as shown in FIG. 12 B. As illustrated in FIG. 12B, the distal end portion and the proximal end portion of the guide extend away from the shaft portion of the guide to extend the guide away from the fixation plate, which provides a space between the fixation plate and the guide in which the tissue is disposed when the guide is removably coupled to the fixation plate.

After removably coupling the guide to the fixation plate, the method 1100 includes, at 1130, providing one or more fixation devices into at least a portion of the bone. In an embodiment, the method 1100 may include, at 1132, pre-drilling one or more holes into the bone using the guide. During the providing, each of the one or more fixation devices may be directed into one of the one or more holes pre-drilled into the bone. For example, at 1134, the method includes providing one or more Kirschner wires. At least one of the one or more fixation devices may pass through the tissue during the providing. As explained above, providing a fixation device through the tissue, rather than cutting the tissue so that the fixation plate can be seen directly, may reduce the damage caused to the tissue during the providing of fixation of the bone fracture.

Subsequently, the method 1100 includes, at 1140, decoupling the guide from the fixation plate. Once the guide has been removed, the method 1100 may include, providing one or more additional fixation devices. The one or more additional fixation devices may comprise one or more screws. In an embodiment, the one or more screws may comprise cannulated screws, where the Kirschner wires (K-wires) are used to guide the screws to the one or more pre-drilled holes, and then the K-wires may be removed. In an embodiment where cannulated screws are provided, the method may include using a cannulated drill to pre-drill holes to receive the cannulated screws. The cannulated drill may utilize the K-wires as guides to pre-drill the holes prior to providing the cannulated screws. The fixation plate may have a thickness configured to retain a head of the screw within the thickness of the fixation plate so that the head of the screw resides within the thickness of the fixation plate once inserted to the appropriate depth. This may prevent irritation of the tissue.

It should be understood that the present system, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the disclosed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

Although the embodiments of the present disclosure and their advantages have been described in detail, it should be understood that various changes, substitutions and alterations can be made herein without departing from the spirit and scope of the disclosure as defined by the appended claims. Moreover, the scope of the present disclosure is not intended to be limited to the particular embodiments of the process, machine, manufacture, composition of matter, means, methods and steps described herein. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A bone fixation system configured to reduce damage to tissue proximate a portion of a bone during fixation of a fracture in the bone, the bone fixation system comprising:
    a fixation plate comprising a head portion, a shaft portion, and a plurality of openings configured to receive one or more fixation devices; and
    a guide comprising a distal end portion, a shaft portion, a proximal end portion, and a plurality of guide openings, wherein the guide is configured to be removably coupled to the fixation plate, and wherein the plurality of guide openings are configured to guide the one or more fixation devices into corresponding ones of the plurality of openings of the fixation plate to provide fixation of the fracture,
    wherein the fixation plate is configured to permit the fixation plate to slide between a surface of the bone and the tissue such that at least a part of the head portion and a part of shaft portion of the fixation plate extend beyond the tissue, wherein the guide is removably coupled to the fixation plate at the part of the head portion and the part of the shaft portion that are configured to extend beyond the tissue, and wherein, when the guide is removably coupled to the fixation plate, the tissue is disposed in a space between the fixation plate and the distal end portion, the shaft portion, and the proximal end portion of the guide.

2. The bone fixation system of claim 1, wherein the bone is a radius bone, and the tissue is a pronator quadratus muscle.

3. The bone fixation system of claim 1, wherein the one or more fixation devices comprise Kirschner wires, screws, rods, or a combination thereof.

4. The bone fixation system of claim 1, wherein the guide comprises one or more pins, wherein the fixation plate comprises one or more pin openings configured to receive the one or more pins to removably couple the guide to the fixation plate.

5. The bone fixation system of claim 4, wherein the one or more pins are retained in the one or more pin openings via a compression fit, a snap fit, or a combination thereof.

6. The bone fixation system of claim 1, wherein the distal end portion and the proximal end portion of the guide extend away from the shaft portion of the guide to extend the guide away from the fixation plate to provide the space between the fixation plate and the guide in which the tissue is disposed when the guide is removably coupled to the fixation plate.

7. The bone fixation system of claim 1, wherein the plurality of openings of the fixation plate are cross-threaded to reduce a likelihood that the one or more fixation devices back out of the bone.

8. The bone fixation system of claim 1, wherein the plurality of openings of the fixation plate comprise a material that is softer than a material used to form a bone screw, and wherein, as the bone screw is screwed into pieces of the fractured bone, the bone screw deforms the softer material of one of the plurality of openings of the fixation plate to lock the bone screw in place and prevent the bone screw from backing out.

9. The bone fixation system of claim 1, wherein each guide opening of the plurality of guide openings corresponds to one of the plurality of openings of the fixation plate and is configured to guide a particular one of the one or more fixation devices into a corresponding one of the plurality of openings of the fixation plate.

10. The bone fixation system of claim 9, wherein at least one of the plurality of guide openings resides, at least in part, within another one of the plurality of guide openings.

11. The bone fixation system of claim 9, wherein different ones of the plurality of guide openings are oriented at different angles.

12. The bone fixation system of claim 10, wherein the different angles are configured to orient fixation devices through the fixation plate and into different portions of the bone to provide multiple points of fixation.

13. The bone fixation system of claim 1, wherein at least one of the one or more fixation devices comprises a screw, and wherein the fixation plate comprises a thickness configured to retain a head of the screw within the thickness of the fixation plate, wherein retention of the head of the screw within the thickness of the fixation plate prevents irritation of the tissue.

14. The bone fixation system of claim 1, wherein the plurality of openings of the fixation plate comprises at least one slot opening, the at least one slot opening configured to receive a fixation device of the one or more fixation devices and thereafter enable slidable adjustment of the fixation plate.

15. The bone fixation system of claim 1, wherein at least one of the one or more fixation devices is configured to pass through the tissue prior to being received by the fixation plate.

16. A method for providing fixation of a fracture of a bone using a bone fixation system configured to reduce damage to tissue proximate a portion of the bone during the providing of the fixation, the method comprising:
    sliding a fixation plate between a surface of the bone and the tissue, wherein the fixation plate comprises a head portion, a shaft portion, and a plurality of openings configured to receive one or more fixation devices, wherein at least a part of the head portion and a part of shaft portion of the fixation plate extend beyond the tissue;
    removably coupling a guide to the fixation plate, wherein the guide comprises a distal end portion, a shaft portion, a proximal end portion, and a plurality of guide openings, wherein the guide is removably coupled to the fixation plate at the part of the head portion and the part of the shaft portion that extend beyond the tissue, wherein, when the guide is removably coupled to the fixation plate, the tissue is disposed in a space between the fixation plate and the distal end portion, the shaft portion, and the proximal end portion of the guide;

providing the one or more fixation devices into at least a portion of the bone, wherein each of the one or more fixation devices passes through at least one of the plurality of guide openings and at least one of the plurality of openings of the fixation plate during the providing the one or more fixation devices.

17. The method of claim 16, further comprising pre-drilling one or more holes into the bone using the guide, wherein, during the providing the one or more fixation devices, each of the one or more fixation devices is directed into one of the pre-drilled one or more holes, wherein at least one of the one or more fixation devices comprises a screw, and wherein the fixation plate comprises a thickness configured to retain a head of the screw within the thickness of the fixation plate, wherein retention of the head of the screw within the thickness of the fixation plate prevents irritation of the tissue.

18. The method of claim 16, wherein at least one of the one or more fixation devices passes through the tissue during the providing the one or more fixation devices.

19. The method of claim 16, wherein the distal end portion and the proximal end portion of the guide extend away from the shaft portion of the guide to extend the guide away from the fixation plate to provide the space between the fixation plate and the guide in which the tissue is disposed when the guide is removably coupled to the fixation plate.

20. The method of claim 16, further comprising decoupling the guide from the fixation plate.

\* \* \* \* \*